US011018954B1

United States Patent
Klein et al.

(10) Patent No.: US 11,018,954 B1
(45) Date of Patent: May 25, 2021

(54) QUEUE PRIORITIZATION SYSTEM FOR MANAGING LANGUAGE INTERPRETATION SERVICES

(71) Applicant: Language Line Services, Inc., Monterey, CA (US)

(72) Inventors: Scott W. Klein, Carmel, CA (US); Jeffrey Cordell, Carmel, CA (US); Lindsay D'Penha, Carmel, CA (US)

(73) Assignee: Language Line Services, Inc., Monterey, CA (US)

( * ) Notice: Subject to any disclaimer, the term of this patent is extended or adjusted under 35 U.S.C. 154(b) by 0 days.

(21) Appl. No.: 16/686,575

(22) Filed: Nov. 18, 2019

(51) Int. Cl.
*G06F 3/0484* (2013.01)
*H04L 12/24* (2006.01)
*H04L 29/08* (2006.01)
*G06Q 10/06* (2012.01)
*G06Q 50/26* (2012.01)
*G06Q 20/12* (2012.01)
*G16H 80/00* (2018.01)

(52) U.S. Cl.
CPC ............ *H04L 41/22* (2013.01); *G06F 3/0484* (2013.01); *G06Q 10/06316* (2013.01); *G06Q 20/127* (2013.01); *G06Q 50/265* (2013.01); *H04L 67/141* (2013.01); *G16H 80/00* (2018.01)

(58) Field of Classification Search
CPC ..... H04L 41/22; H04L 67/141; G06Q 20/127; G06Q 50/265; G06Q 10/06316; G06F 3/0484; G16H 80/00
See application file for complete search history.

(56) References Cited

U.S. PATENT DOCUMENTS

2017/0046337 A1* 2/2017 Cordell ............... G06Q 10/0631
2019/0057326 A1* 2/2019 Li ........................... G06Q 10/02

OTHER PUBLICATIONS

Panagiotis D. Ritsos et al., Using Virtual Reality for Interpreter-mediated Communication and Training, Sep. 1, 2012, IEEE Xplore, pp. 191-198 (Year: 2012).*
Sheila Mugala et al., Glove Based Sign Interpreter for Medical Emergencies, May 1, 2019, IEEE Xplore, pp. 1-8 (Year: 2019).*

* cited by examiner

*Primary Examiner* — Tam T Tran
(74) *Attorney, Agent, or Firm* — Patent Ingenuity, P.C.; Samuel K. Simpson

(57) ABSTRACT

A process generates, at a language interpretation platform, a graphical user interface that manages a connection time between a user-operated device and a language interpreter-operated device. Further, the process receives, from the graphical user interface of the user-operated device, a request for a live language interpretation session. The process determines, from the graphical user interface of the user-operated device, an activation of a queue prioritization status. The activation is selected from the group consisting of: an automatic account activation, a user-inputted activation via a virtual indicium in the graphical user interface, and an environmental activation. Finally, the process assigns, to the graphical user interface of the user-operated device, the prioritization status to the user-operated device to prioritize the connection time in a queue of waiting devices.

20 Claims, 12 Drawing Sheets

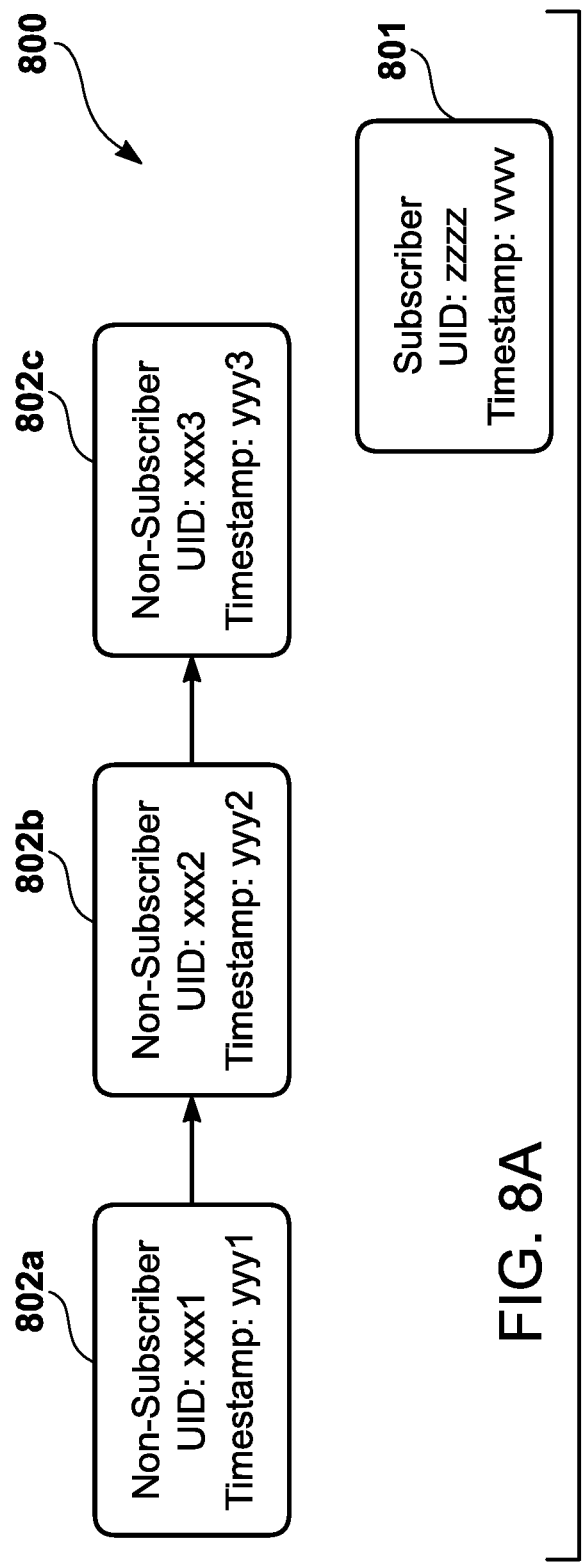
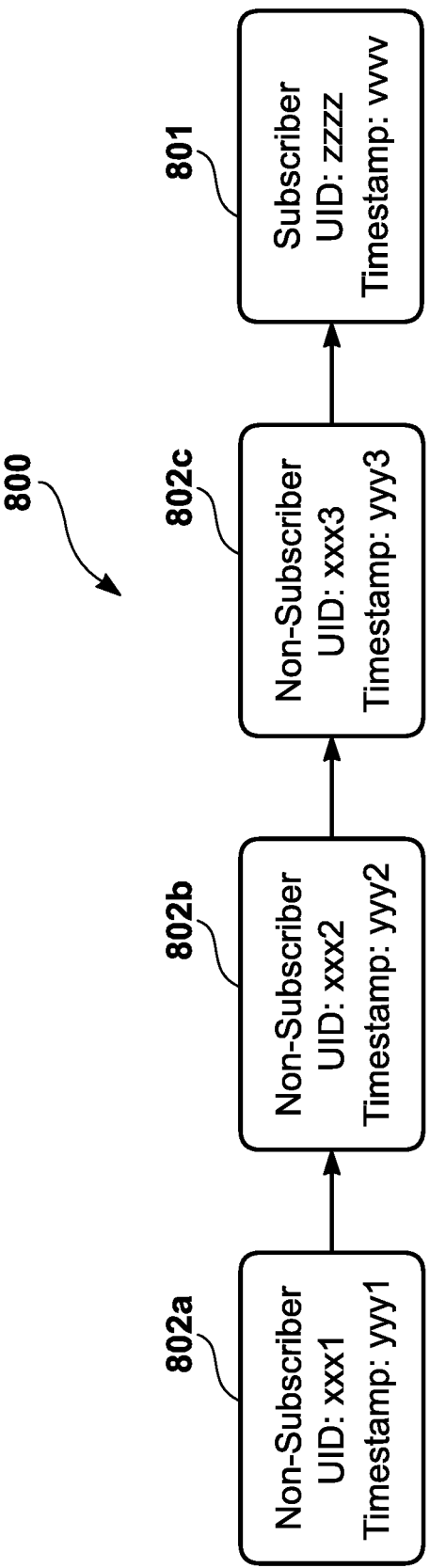
FIG. 8A
FIG. 8B

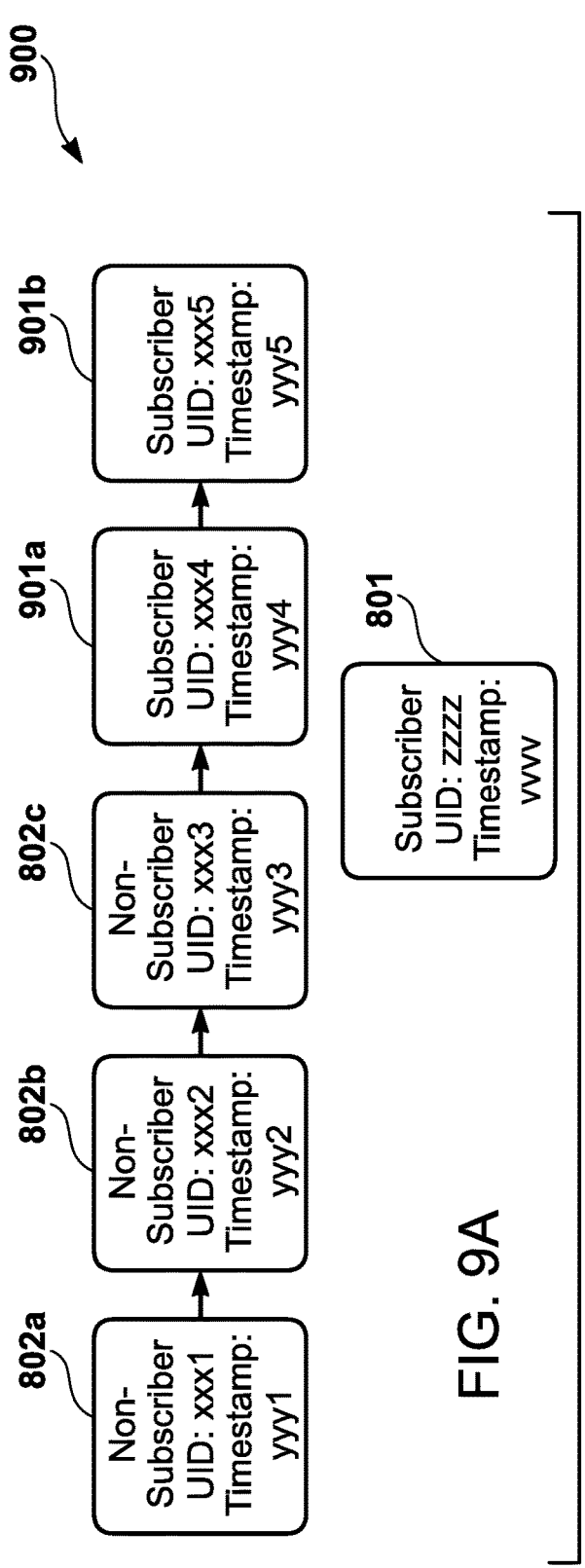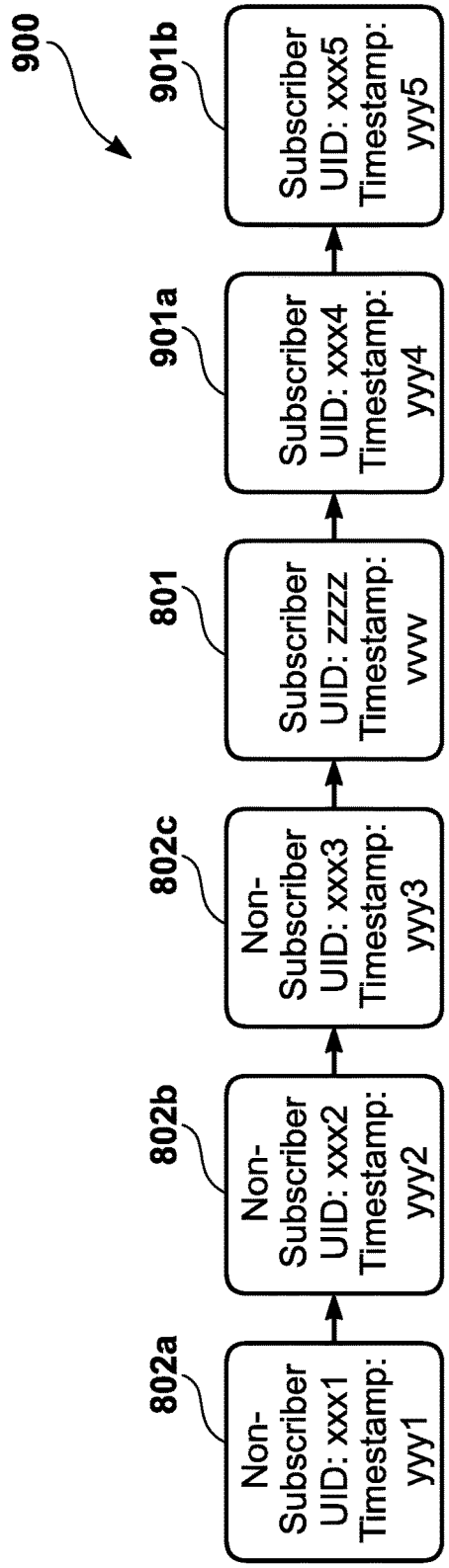
FIG. 9A
FIG. 9B

QUEUE PRIORITIZATION SYSTEM FOR MANAGING LANGUAGE INTERPRETATION SERVICES

BACKGROUND

1. Field

This disclosure generally relates to the field of language interpretation. More particularly, the disclosure relates to language interpretation services offered on a computerized platform.

2. General Background

Language interpretation services may play a critical role in certain environments (e.g., a medical environment). For instance, a first human user (e.g., a doctor), who speaks a first human-spoken language (i.e., a language that is traditionally spoken by a group of people originating from a particular geographical location, country, or region) such as English, may want to have a conversation with a second human user (e.g., a patient), who speaks a second human-spoken language, such as Spanish (referred to herein as a limited English proficiency speaker ("LEP")).

A typical approach is to have a face-to-face in-person language interpretation performed by an on-site language interpreter. For example, while in a hospital room with the patient, the doctor may place a telephone call to the hospital administrative staff to request that an on-site language interpreter be present during the conversation between the doctor and the patient. The on-site language interpreter would go to the hospital room, listen to the doctor speak in English, translate what the doctor said into Spanish for the benefit of the patient, listen to the patient's response in Spanish, and translate what the patient said in Spanish into English; such dialogue may occur until the completion of the conversation between the doctor and the patient so that the doctor can effectively treat the patient. However, the on-site language interpreter may not have availability, or may not even be present within the hospital, at the time of the doctor's request (e.g., late evening hours). Further, even if the on-site language interpreter can be immediately available, he or she may not be conversant in the language spoken by the patient (e.g., a language not commonly spoken). As a result, the face-to-face approach has limited efficacy, and is not robust enough for an organization (e.g., a hospital) that may necessitate urgent language interpretation service at a moment's notice.

To alleviate the difficulties posed by the face-to-face approach, some organizations opt to use over the phone interpretation ("OPI") as a supplement, or as an alternative. For example, a language interpretation service provider may provide the OPI service remotely from the hospital such that the doctor or the patient may use a communication device (e.g., telephone, smartphone, tablet device, etc.) to establish a voice-based language interpretation session with a language interpreter through the language interpretation service provider. As yet another alternative, the language interpretation service provider may provide a video remote interpretation ("VRI") service, which allows users to establish a video-based language interpretation session via a computing device (e.g., personal computer ("PC"), laptop computer, smartphone, tablet device, smartwatch, etc.) with a remotely situated language interpreter via the language interpretation service provider.

Although the foregoing alternative approaches have allowed users to potentially obtain access to a language interpreter for a live, language interpretation session faster than when an on-site language interpreter speaking both languages to be interpreted is not available, such approaches are susceptible to delays. For example, upon receiving an OPI session request or a VRI session request, the language interpretation service may have a backlog of requests, and may not be able to immediately connect the users to a remotely situated language interpreter that is qualified to perform the language interpretation in the amount of time necessitated by the users in the particular environment from which the request is placed. Therefore, current language interpretation configurations do not adequately manage backlog requests for remote language interpretation sessions.

SUMMARY

A process generates, at a language interpretation service platform, a graphical user interface ("GUI") that manages a connection time between a user-operated device and a language interpreter-operated device. Further, the process receives, from the GUI of the user-operated device, a request for a live language interpretation session. The process determines, from the GUI of the user-operated device, an activation of a queue prioritization status. The activation is selected from the group consisting of: an automatic account activation, a user-inputted activation via a virtual indicium in the GUI, and an environmental activation. Finally, the process assigns, to the GUI of the user-operated device, the prioritization status to the user-operated device to prioritize the connection time in a queue of waiting devices.

As another alternative, a computer program may have a computer readable storage device with a computer readable program stored thereon that implements the functionality of the aforementioned process. As yet another alternative, a computerized language interpretation platform may implement the functionality of the aforementioned process. Finally, as another alternative, a mobile computing device may implement the functionality of the aforementioned process.

BRIEF DESCRIPTION OF THE DRAWINGS

The above-mentioned features of the present disclosure will become more apparent with reference to the following description taken in conjunction with the accompanying drawings wherein like reference numerals denote like elements and in which:

FIG. 8A illustrates the queue data structure being a linked list in which one or more pointers are used to reference other data blocks.

FIG. 8B illustrates the queue prioritization engine inserting the data block at the front of the queue data structure corresponding to the English/Spanish language interpreter.

FIG. 9A illustrates the queue data structure being a linked list with both data blocks corresponding to existing non-subscriber users and data blocks corresponding to existing subscriber users within the English/Spanish queue.

FIG. 9B illustrates the queue prioritization engine inserting the data block in front of the non-subscriber data blocks, but behind the existing subscriber data blocks.

DETAILED DESCRIPTION

Figure 1A:
FIG. 1A illustrates an example of a physical environment being a natural disaster involving a fire that is approaching a structure, such as a home.

A queue prioritization configuration is provided to manage language interpretation services. In particular, the queue prioritization configuration assigns a prioritization status to a device, account, and/or first responder based on an account activation, user activation, and/or environmental activation. In other words, a user is allowed to move ahead of other users already in the queue based on the assignment of such prioritization status. In effect, the queue prioritization configuration allows for activation (automatic or user-inputted) to prioritize connection to a language interpreter for one user over other users in certain instances, and to validate such prioritization. For example, in the case of a natural disaster, a first responder in the midst of helping various people should not have to wait on hold a relatively long time for a language interpreter to interpret/translate a conversation with an LEP that is in need of evacuation. Accordingly, the queue prioritization configuration prioritizes connection of the first responder to a language interpreter over users that were already present in the queue. Furthermore, to avoid fraudulent prioritization invocation, the queue prioritization configuration may validate that the first responder is within a natural disaster area by performing a geolocation assessment based on one or more geographical coordinates received from a device operated by a user and/or first responder.

The foregoing first responder example is only one example of queue prioritization being invoked by an activation from a device, account, or first responder. As another example, a device may operate a software application that has a device setting corresponding to a subscription, which may be fee-based. By interacting with the device via one or more user inputs (e.g., touch-based, voice, gestures, etc.), the user may indicate that the queue prioritization configuration should automatically be activated any time the user uses the software application to request a language interpreter. As a result, the queue prioritization configuration is automatically configured to move the user in front of users presently in the queue, but that don't have a prioritization status. (The term "device" is intended to refer to a computing device (e.g., smartphone, tablet device, personal computer ("PC"), laptop computer, etc.), communication device (wearable, hand-held, stationary, etc.), or any other device that allows the user to invoke the queue prioritization configuration.) As yet another example, the user may not have activated a device setting corresponding to a subscription, but may invoke an on-demand queue prioritization status via a visual indicium (e.g., a virtual button). The invocation of such visual indicium may be an environmental activation, just as in the case of a first responder. Alternatively, the invocation of the visual indicium may be fee-based. In another embodiment, the button may be a physical button that is positioned on a communication device.

As yet another alternative, an organization may obtain automatic queue prioritization status for its users by obtaining a subscription, which may be fee-based, to the queue prioritization service. In other words, the subscription activation may be invisible to the user (e.g., inaccessible via a device setting on a device operated by the user). The queue prioritization status effectively allows the participant to move ahead of non-subscribers already in the queue when the participant provides the request for the language interpretation session. From an organizational perspective, the queue prioritization configuration allows an organization (e.g., hospital, financial institution, insurance company, etc.) to obtain on-demand priority for a live language interpretation service at a moment's notice. Having such an on-demand language interpretation service, which is not hindered by human resource availability and/or times of the day, allows the organization to forego on-site staffing problems. The organization can effectively plan for spontaneous language interpretation requests.

Figure 1B:
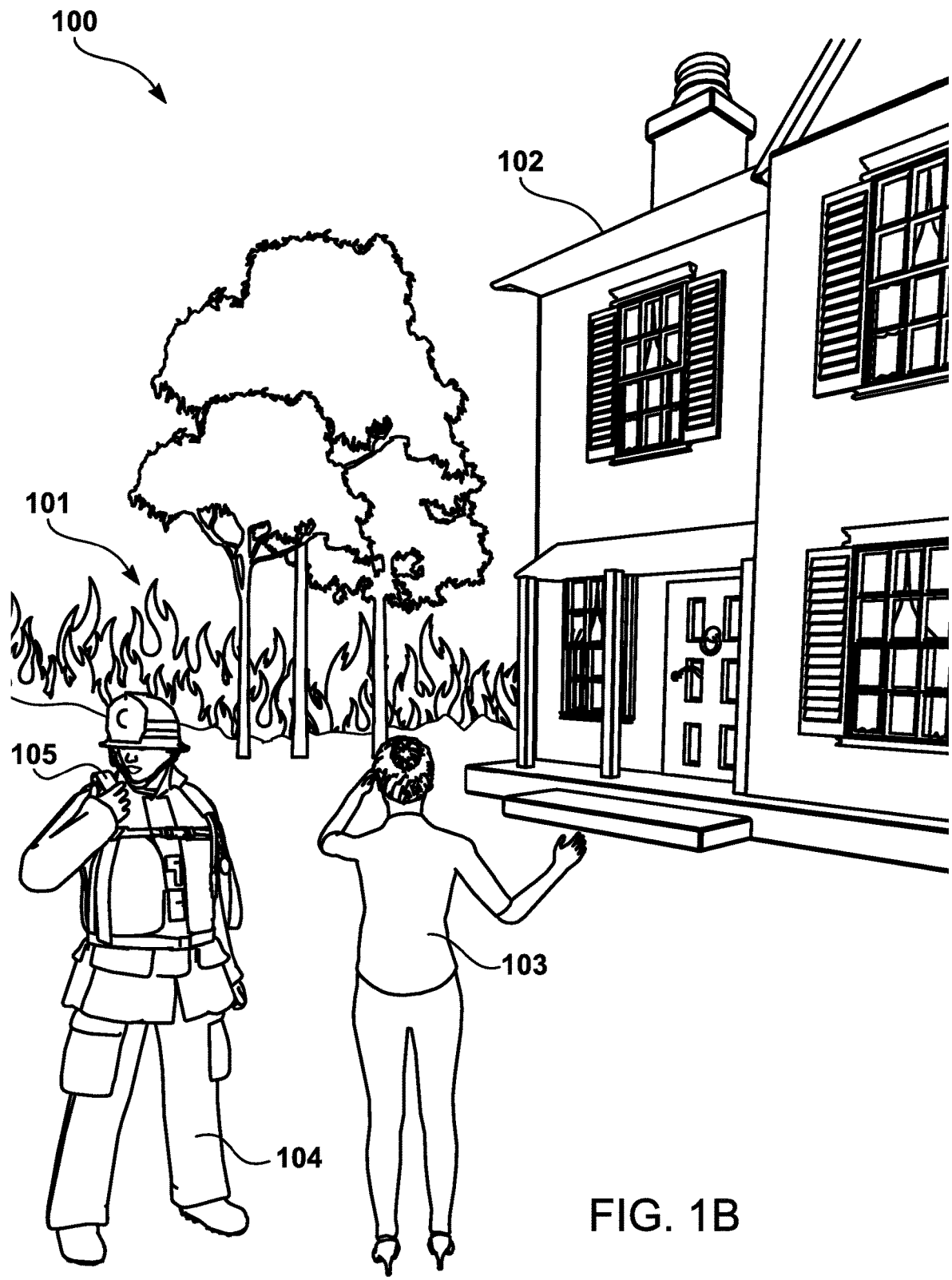
FIG. 1B illustrates another example of the physical environment, but with first responder utilizing a communication device that is not a computing device.

FIGS. 1A and 1B illustrate an example of a physical environment 100 that is the site of an emergency situation in which language interpretation services are needed. For instance, FIG. 1A illustrates an example of the physical environment 100 being a natural disaster involving a fire 101 that is approaching a structure 102, such as a home. A resident 103 of the home may have requested that a first responder 104 (e.g., fireman) assist her with evacuation and/or preventing damage to her home. The resident 103 may be an LEP, who has difficulty communicating with the first responder 104 in English. Accordingly, the first responder 104 may utilize a mobile computing device 105 to access a language interpretation service (e.g., via a software application). A remotely situated language interpreter may then provide language interpretation services through the mobile computing device to translate the communications between the first responder 104, who speaks a first language (e.g., English), and the resident 103, who speaks a second language (e.g., Spanish). The language interpretation session may be established via a variety of different modalities (e.g., video, voice, etc.). FIG. 1B illustrates another example of the physical environment 100, but with the first responder 104 utilizing a communication device 155 (e.g., radio (wearable or handheld)) that is not considered a computing device.

In emergency situations, such as those illustrated in FIGS. 1A and 1B, the queue prioritization configuration may prioritize the connection time of the first responder 104 and/or the resident 103 to a language interpreter for a live language interpretation session. In other words, the queue prioritization configuration may allow for prioritization of a connection time to a language interpreter based on a variety of account (fee-based subscription), device (user-inputted request for on-demand prioritization), or emergency (user-inputted or environmental detection) activations.

Figure 2A:
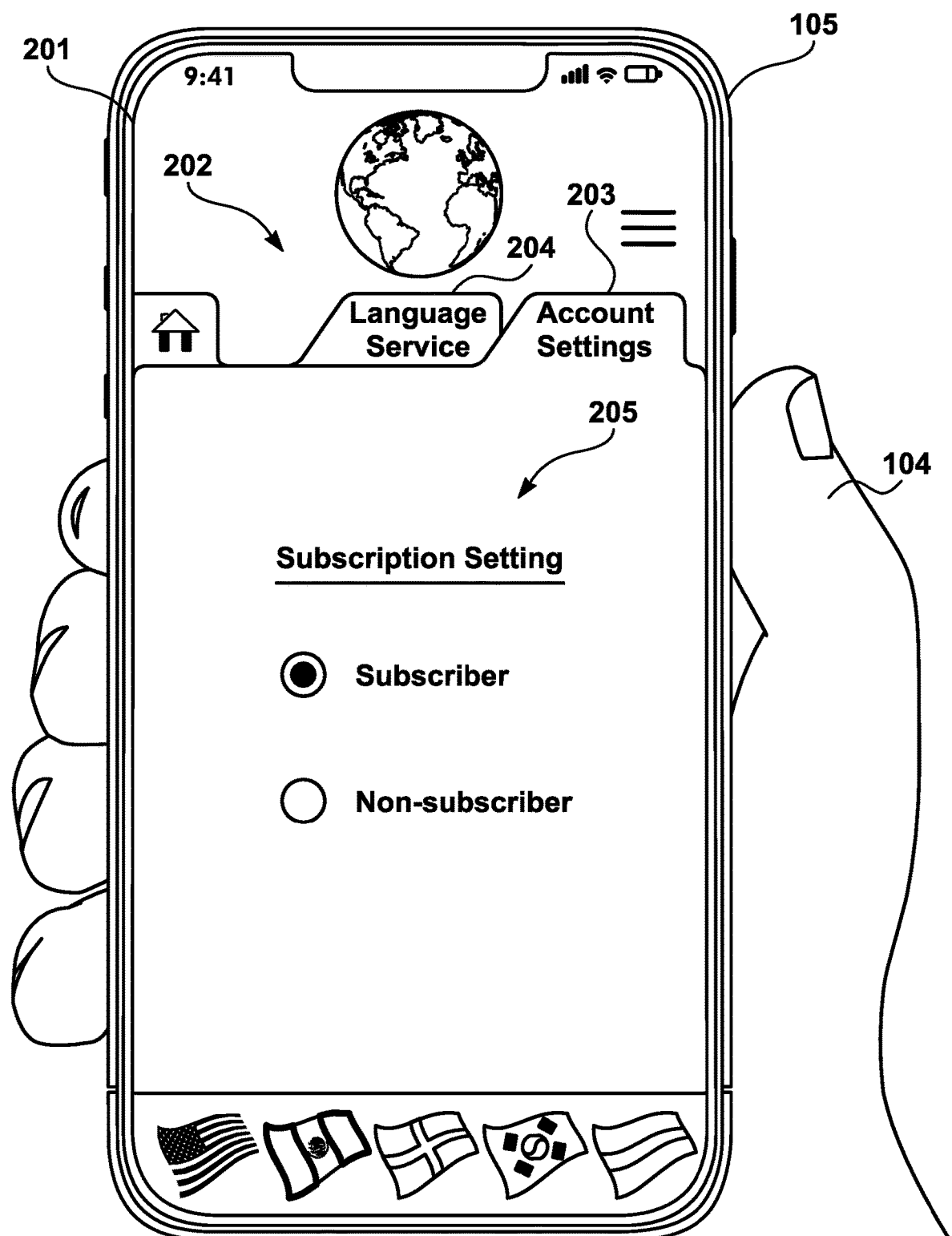
FIG. 2A illustrates the mobile computing device having a display screen that renders a GUI.
Figure 2B:
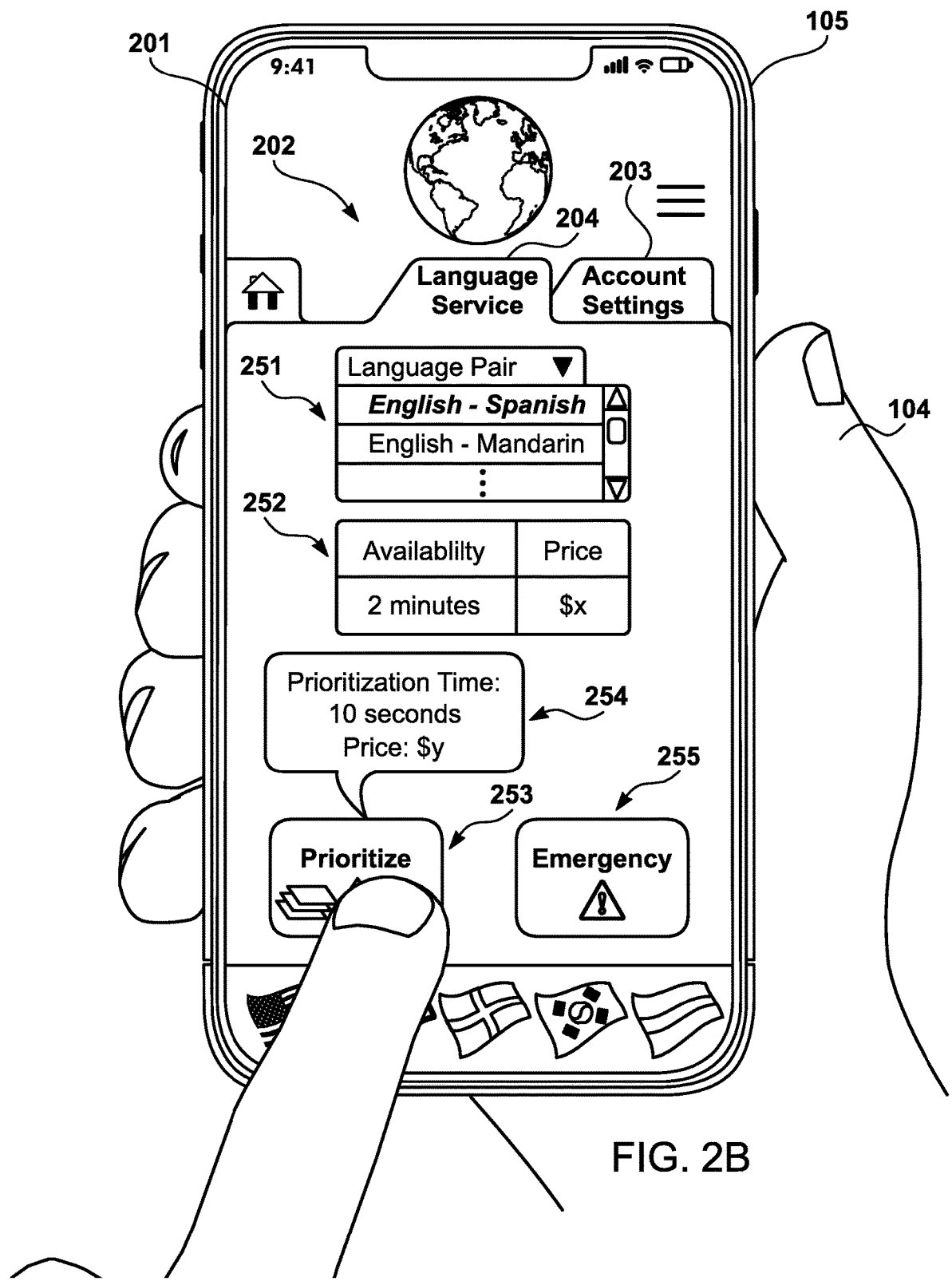
FIG. 2B illustrates the GUI of FIG. 2A displaying a language interpretation service menu.
Figure 2C:
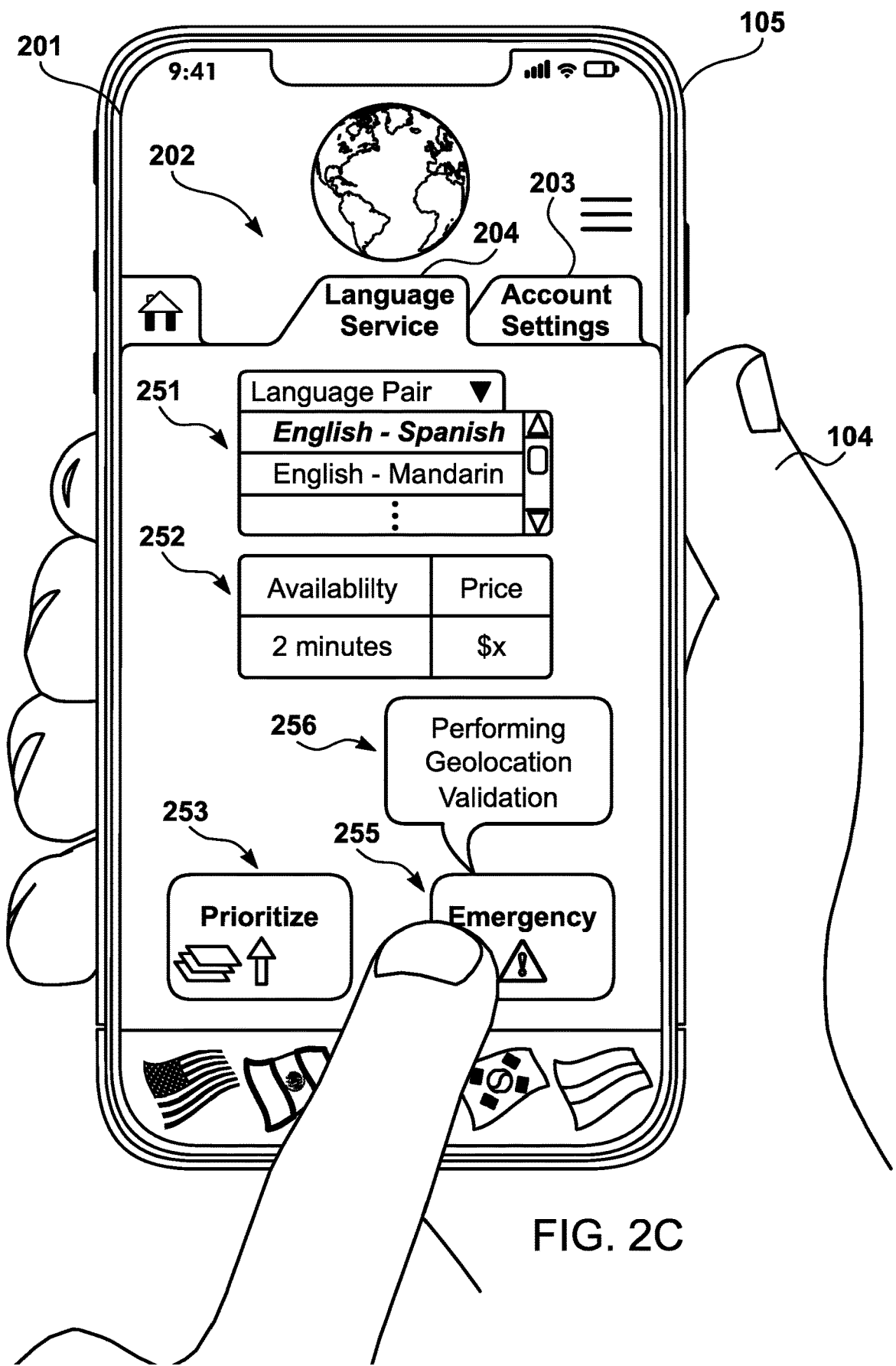
FIG. 2C illustrates the GUI of FIG. 2A displaying a language interpretation service menu that has an emergency indicium.

FIGS. 2A-2C illustrates examples of a GUI 202 that may be rendered, on a display screen 201, by a software application executed by a processor of the mobile computing device 105 illustrated in FIG. 1A. For example, FIG. 2A illustrates the mobile computing device 105 having the display screen 201 that renders the GUI 202. In particular, the GUI 202 may be rendered to display various category indicia, such as an account settings category indicium 203. FIG. 2A illustrates the first responder 104, or potentially a non-first responder user, viewing the account settings to select from a subscription settings menu 205. For example, a user may select an account setting for a fee-based subscription that allows for automatic queue prioritization for connecting to a language interpreter. As a result, the mobile computing device 105 may have a connection time that is automatically prioritized over other non-subscriber, or other non-prioritized, devices waiting in a queue. Alternatively, the user may select the non-subscriber option, which would place the mobile computing device 105 in the queue without a prioritized connection time based on an account setting.

Additionally, FIG. 2B illustrates the GUI 202 of FIG. 2A displaying a language interpretation service menu. For example, the user may select a language pair (e.g., English-Spanish) from a language pair menu 251 to indicate the language pair in which the language interpreter should have a qualification. The GUI 202 may also display an availability window 252 that indicates the next availability (i.e., the non-subscriber queue wait time) and the price for the next available language interpreter qualified in the language pair. Moreover, the GUI 202 may display a prioritization indicium 253 that allows the user to provide a user input to request prioritization in the queue ahead of other devices in the queue. For example, as indicated by a prioritization pop-up 254 (other indicia may be utilized), the user may pay an additional fee to obtain on-demand prioritization via a user input to the GUI 202.

Moreover, FIG. 2C illustrates the GUI 202 of FIG. 2A displaying a language interpretation service menu that has an emergency indicium 255. In the event of a natural disaster, as illustrated in FIG. 1A, the emergency indicium 255 allows a user (e.g., first responder 104, resident 103, etc.) to provide an on-demand emergency request for prioritization, without an additional fee. To avoid fraudulent activation of the emergency indicium 255 (e.g., by persons not really in an emergency environment), the language interpretation platform may perform a geolocation assessment to validate the presence of the mobile computing device 105 within an emergency environment, as indicated by the geolocation validation pop-up 256 (other indicia may be utilized).

Although a GUI is illustrated in FIGS. 2A-2C, the prioritization activations may be performed via non-visual inputs. For example, the first responder 104 may provide voice-based inputs to the communication device 105. Also, the GUI 202 may only have some of the virtual indicia illustrated in FIGS. 2A-2C.

Figure 3A:
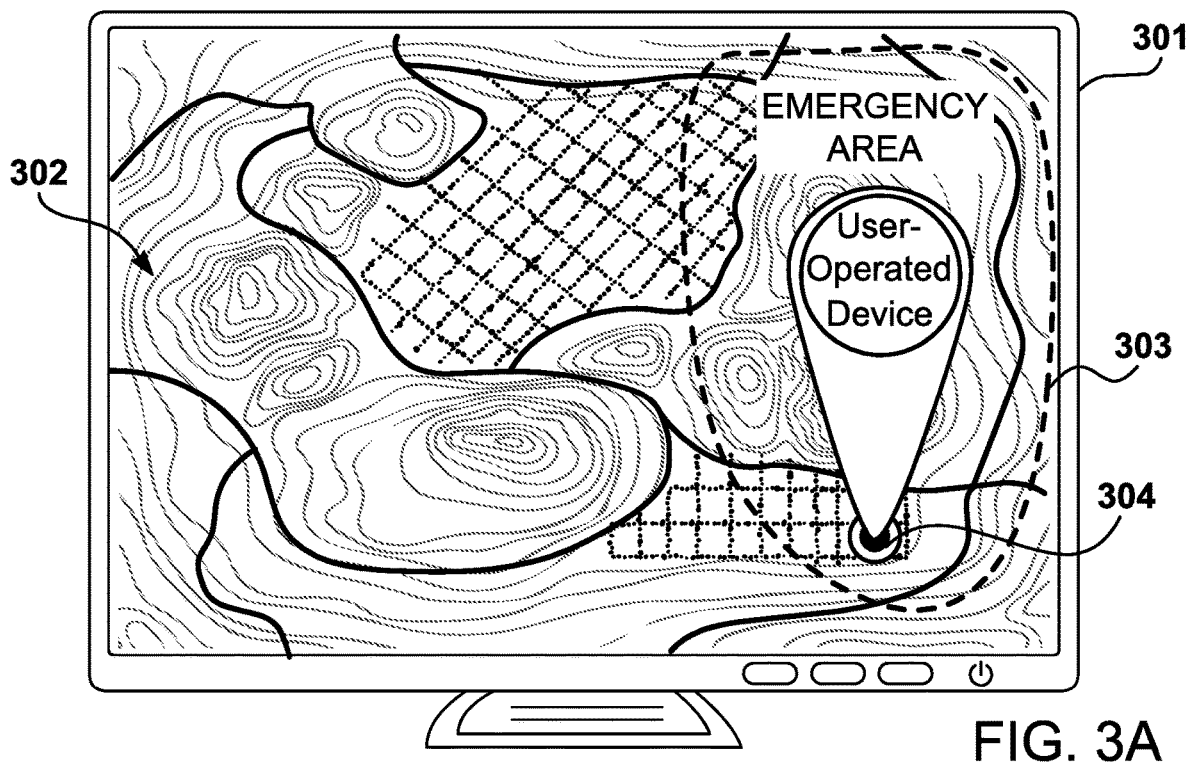
FIG. 3A illustrates a display device, which may be in operable communication with the language interpretation platform, that displays a topographical view of a geographical area that encompasses the emergency area.
Figure 3B:
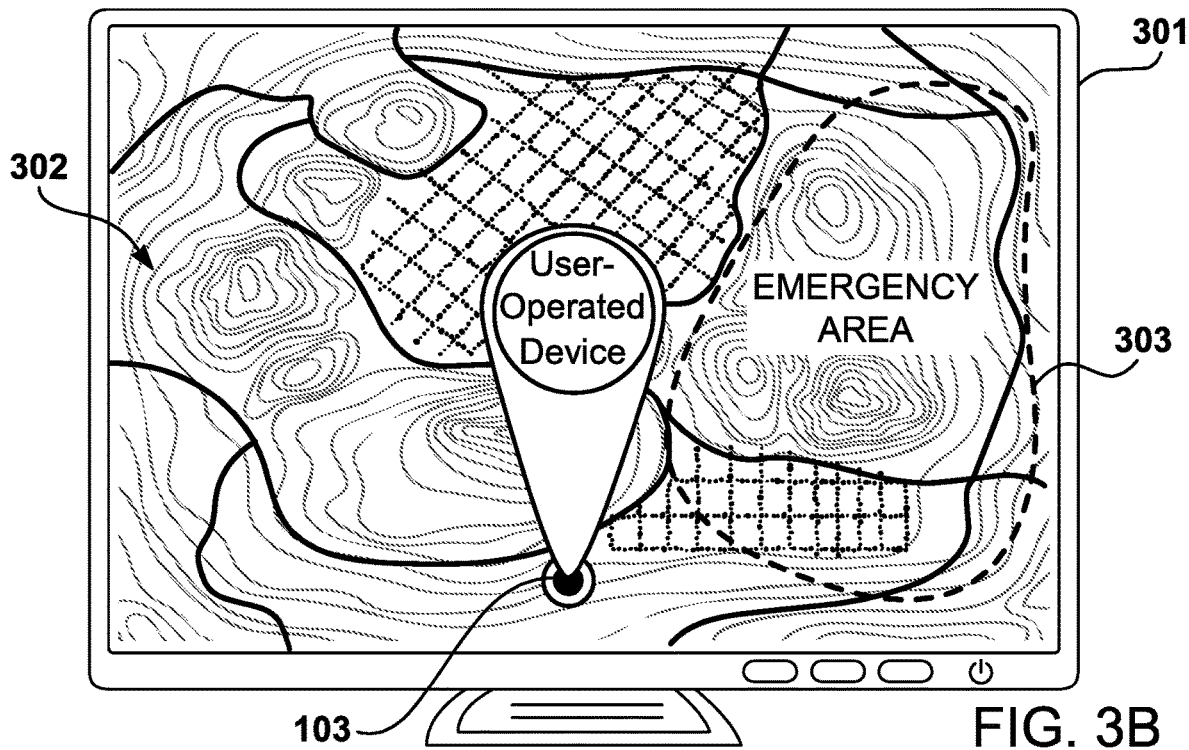
FIG. 3B illustrates the language interpretation system determining that the mobile computing device is not positioned within the emergency area.

FIGS. 3A and 3B illustrate examples of geolocation assessments that may be performed by the language interpretation platform to validate the presence of the mobile computing device 105, illustrated in FIG. 2C, within an emergency environment. For example, FIG. 3A illustrates a display device 301, which may be in operable communication with the language interpretation platform, that displays a topographical view of a geographical area 302 that encompasses the emergency area 303. Furthermore, based on geolocation data (e.g., global positioning system ("GPS") coordinates) received from the mobile computing device 105, the language interpretation platform may perform a comparison to determine whether the received coordinates fall within the coordinates for the emergency area 303. As illustrated in FIG. 3A, the language interpretation system may automatically determine geolocation validation, and allow for non-fee prioritization of the mobile computing device 105. Optionally, the language interpretation system may render the geolocation assessment on the display device 301. Alternatively, as illustrated in FIG. 3B, the language interpretation system may determine that the mobile computing device 105 is not positioned within the emergency area 303. Accordingly, the language interpretation system may reject the request for queue prioritization by the mobile computing device 105.

In an alternative embodiment, the language interpretation platform automatically provides access to a prioritized connection time for devices within the emergency area 303 without a prioritization request from a user. For example, the language interpretation platform may determine, from an external source (e.g., news feed, weather alerts, etc.) that a particular geographical location is an emergency area 303, and may provide automatic prioritization to any devices requesting language interpretation services having GPS coordinates within the emergency area 303, even without a request for prioritization by a user.

Figure 4A:
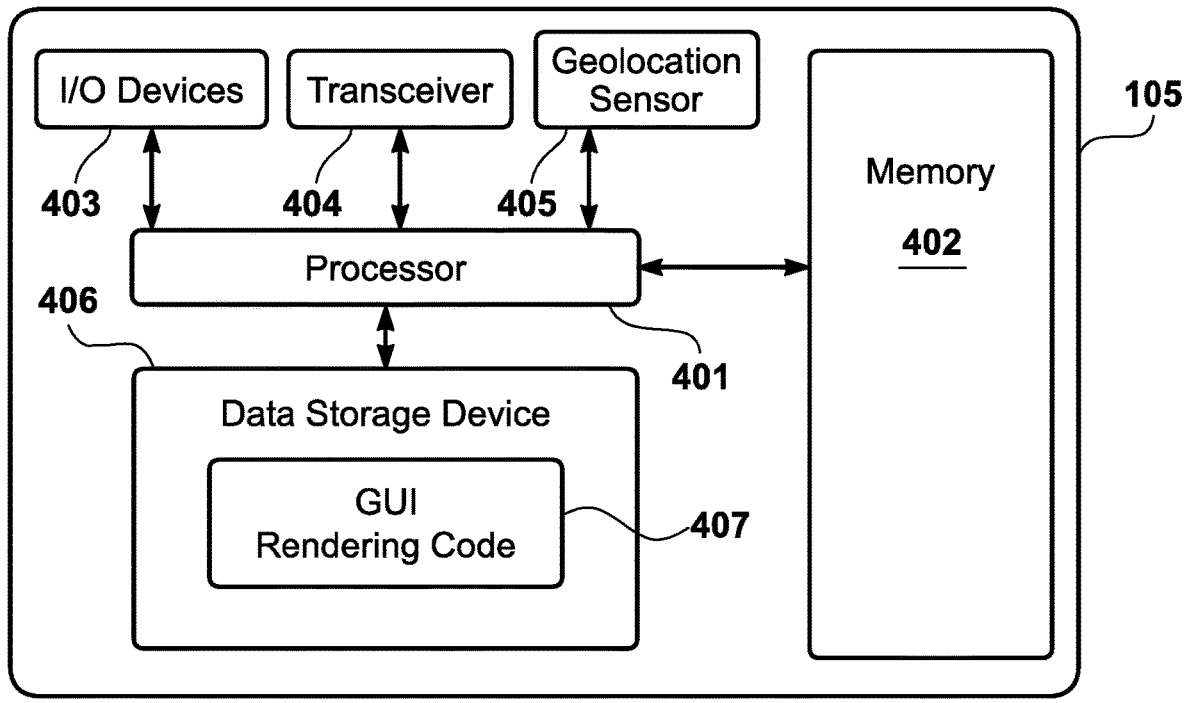
FIG. 4A illustrates a configuration of the internal components of the mobile computing device illustrated in FIG. 1A.
Figure 4B:
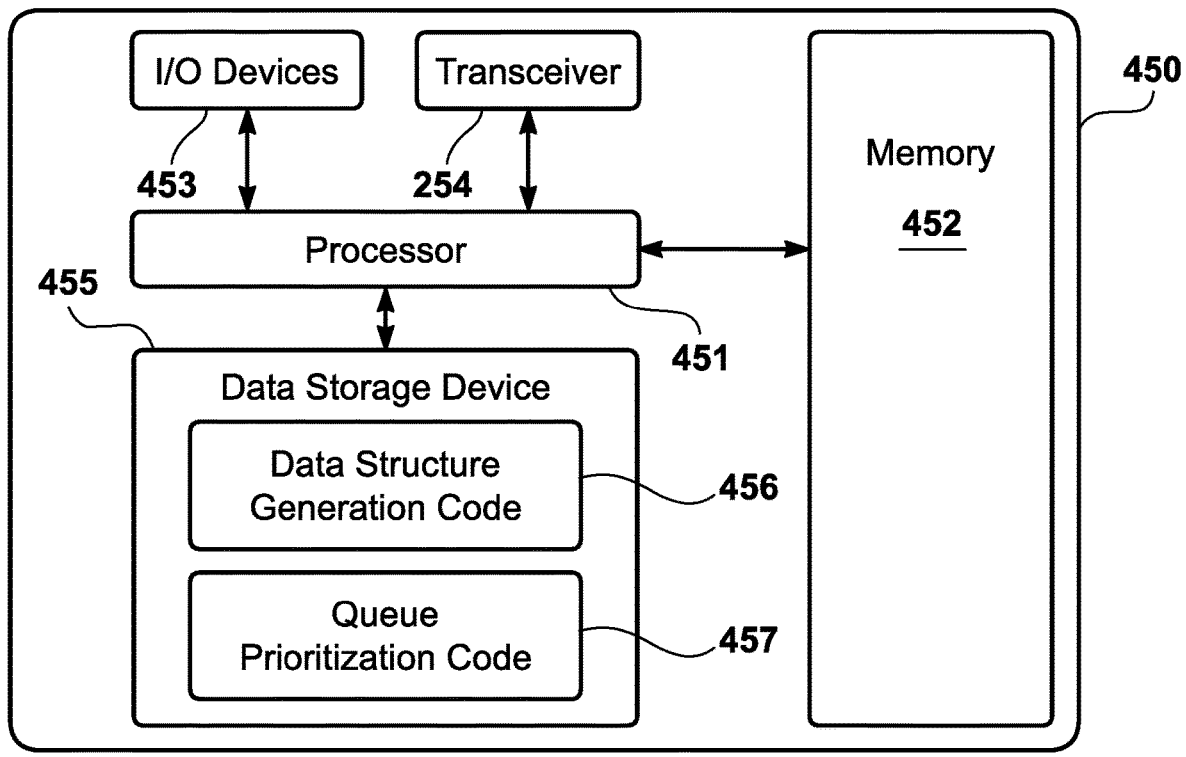
FIG. 4B illustrates a configuration of the internal components of a language interpretation platform that may be utilized to perform queue prioritization based on an activation received via the GUI rendered by the mobile computing device illustrated in FIG. 2A.

FIGS. 4A and 4B illustrate various hardware configurations that may be utilized to implement the queue prioritization system. For instance, FIG. 4A illustrates a configuration of the internal components of the mobile computing device 105 illustrated in FIG. 1A. The mobile computing device 105 may have a processor 401, which may be specialized for generating a GUI. The mobile computing device 105 may also have a geolocation sensor 405 (e.g., GPS device) that determines the geolocation coordinates of the mobile computing device 105. Also, the mobile computing device 105 may also have an input/output ("I/O") device 403 (e.g., keyboard, joystick, microphone, camera, scanner, etc.) that may be used to obtain one or more user inputs. Finally, the mobile computing device 105 may have a transceiver 404 that is used to send and/or receive data through a network. (Alternatively, a separate transmitter and receiver may be used instead.)

Furthermore, the processor 401 may retrieve various code from a data storage device 406 for execution in the memory device 402. For example, the processor 401 may retrieve GUI rendering code 407 from the data storage device 406 to generate the GUI 202 illustrated in FIGS. 2A-2C.

In addition, FIG. 4B illustrates a configuration of the internal components of a language interpretation platform 450 that may be utilized to perform queue prioritization based on an activation received via the GUI 202 rendered by the mobile computing device 105 illustrated in FIG. 2A. The language interpretation platform 450 has a processor 451, which may be specialized for performing queue prioritization within a queue data structure. Furthermore, the language interpretation platform 450 has a memory device 452, which is specialized for storing the queue data structure. For example, the memory device 452 may have specialized capabilities for allocating data in a particular manner to reduce memory requirements.

Furthermore, the processor 451 may retrieve various code from a data storage device 455 for execution in the memory device 452. For example, the processor 451 may retrieve data structure generation code 456 from the data storage device 455 to generate a queue data structure. As another example, the processor 451 may retrieve the queue prioritization code 457 to perform queue prioritization to modify the queue data structure.

Also, the language interpretation platform 450 may also have an I/O device 453 (e.g., keyboard, joystick, microphone, camera, scanner, etc.) that may be used to obtain one or more user inputs. Finally, the language interpretation platform 450 may have a transceiver 454 that is used to send and/or receive data through a network. (Alternatively, a separate transmitter and receiver may be used instead.)

Figure 5:
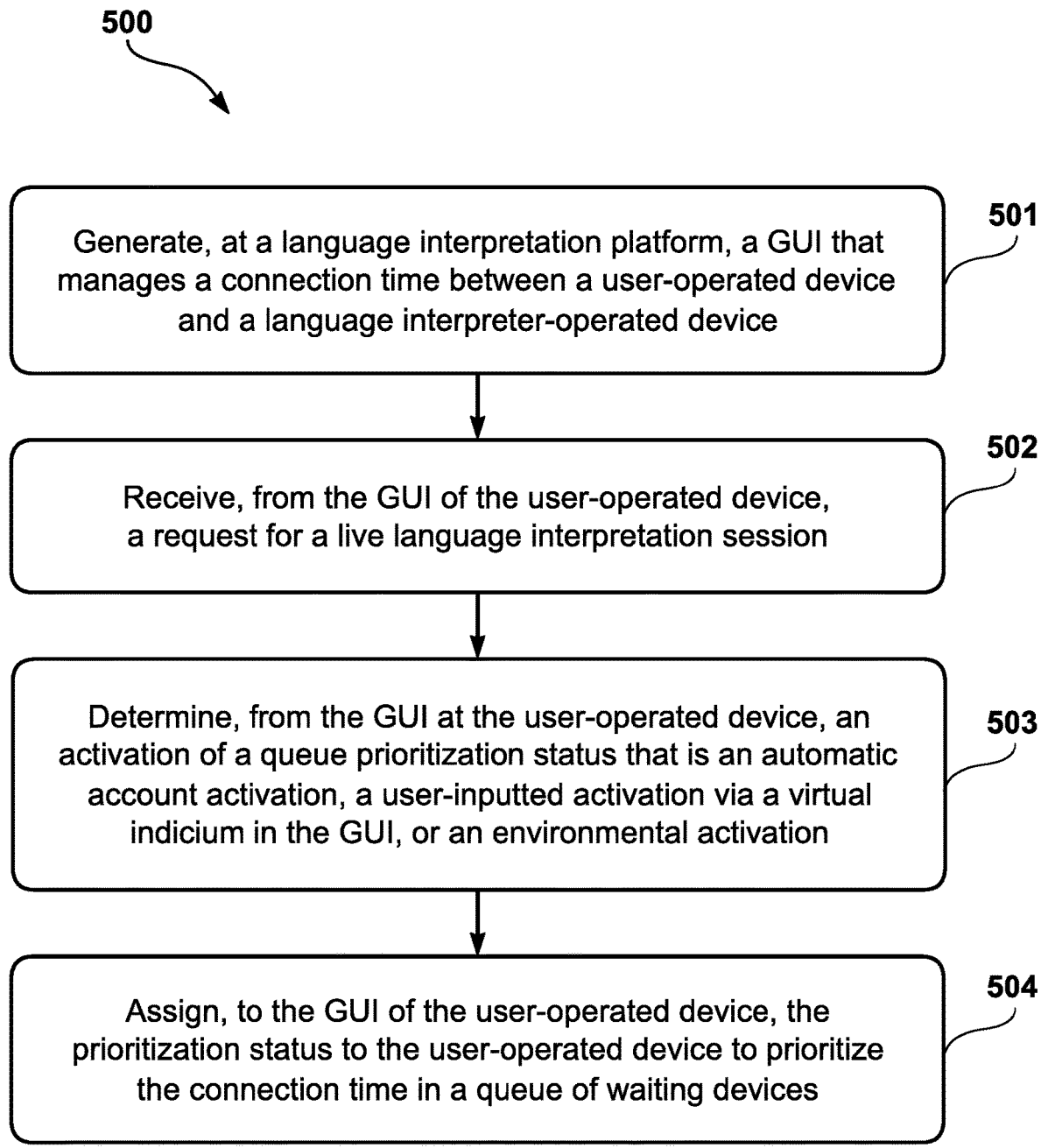
FIG. 5 illustrates a process that may be utilized by the language interpretation platform illustrated in FIG. 4B to provide queue prioritization.

FIG. 5 illustrates a process 500 that may be utilized by the language interpretation platform 450 illustrated in FIG. 4B to provide queue prioritization. At a process block 501, the process 500 generates, at the language interpretation platform 450, the GUI 202, illustrated in FIGS. 2A-2C, that manages a connection time between a user-operated device 105 and a language interpreter-operated device. Further, at a process block 502, the process 500 receives, from the GUI 202 of the user-operated device, a request for a live language interpretation session. Additionally, at a process block 503, the process 500 determines, via the GUI 202 of the user-operated device 105, an activation of a queue prioritization status. The activation is selected from the group consisting of: an automatic account activation, a user-inputted activation via a virtual indicium in the graphical user interface, and an environmental activation. Moreover, at a process block 504, the process 500 assigns, to the GUI 202 of the user-operated device, the prioritization status to the user-operated device to prioritize the connection time in a queue of waiting devices.

Figure 6:
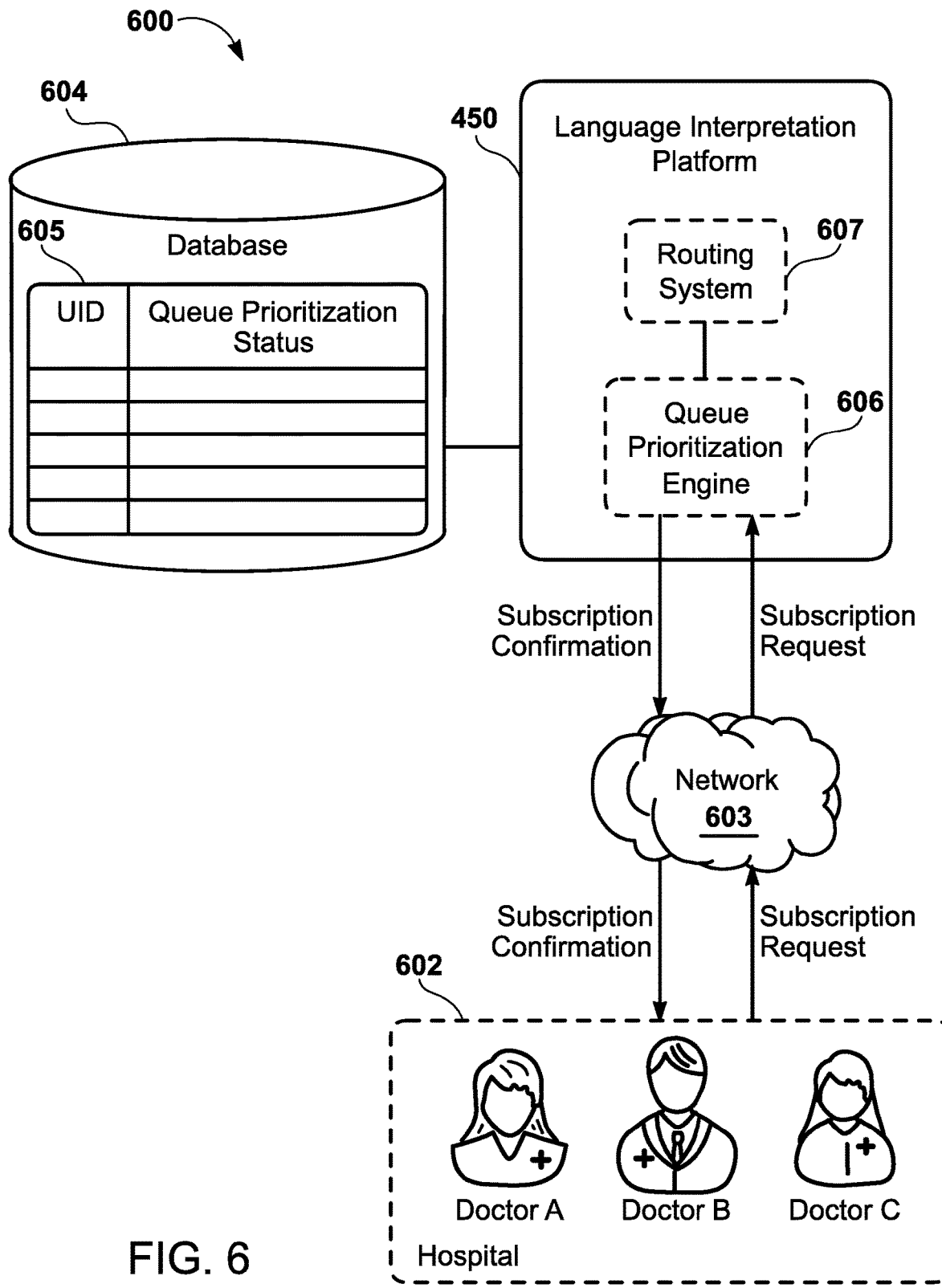
FIG. 6 illustrates a queue prioritization system that may implement the queue prioritization process, illustrated in FIG. 5, via the language interpretation platform.

In one embodiment, as illustrated by FIG. 6, a queue prioritization system 600 may implement the queue prioritization process 500, illustrated in FIG. 5, via the language interpretation platform 450. In particular, the language interpretation platform 450 has a queue prioritization engine 606 that performs queue management. For example, a subscriber 602 may be an entity such as a hospital, which has multiple healthcare practitioners (e.g., doctors) that are in need of language interpretation services on a regular basis. In one embodiment, the subscriber 602 may establish the subscription to the queue prioritization service by sending a request via a network 603 to the queue prioritization engine 606, which may send a subscription confirmation to the subscriber 602. Furthermore, the queue prioritization engine 606 may store queue prioritization subscription data in a routing data structure 605 stored in a database 604, which is in operable communication with the queue prioritization engine 606. In particular, the routing data structure 605 may be a multi-dimensional array. For example, the routing data structure 605 may have various rows, which each correspond to a particular user, as identified by a user id ("UID") column. (Data structures other than a multidimensional array may be used instead for the routing data structure 605.) Furthermore, the routing data structure 605 may have a queue prioritization status, which indicates whether or not the user associated with the particular UID is a subscriber or not. As a result, the queue prioritization engine 606 is able to provide an indication to a routing system 607 as to whether a particular a particular user should be routed ahead of other users based on the queue prioritization status.

In an alternative embodiment, the queue prioritization status of a particular user may be determined in a configuration other than from the routing data structure 605. For example, each user request may have metadata or a tag indicating whether or not a user is a subscriber or a non-subscriber.

Figure 7:
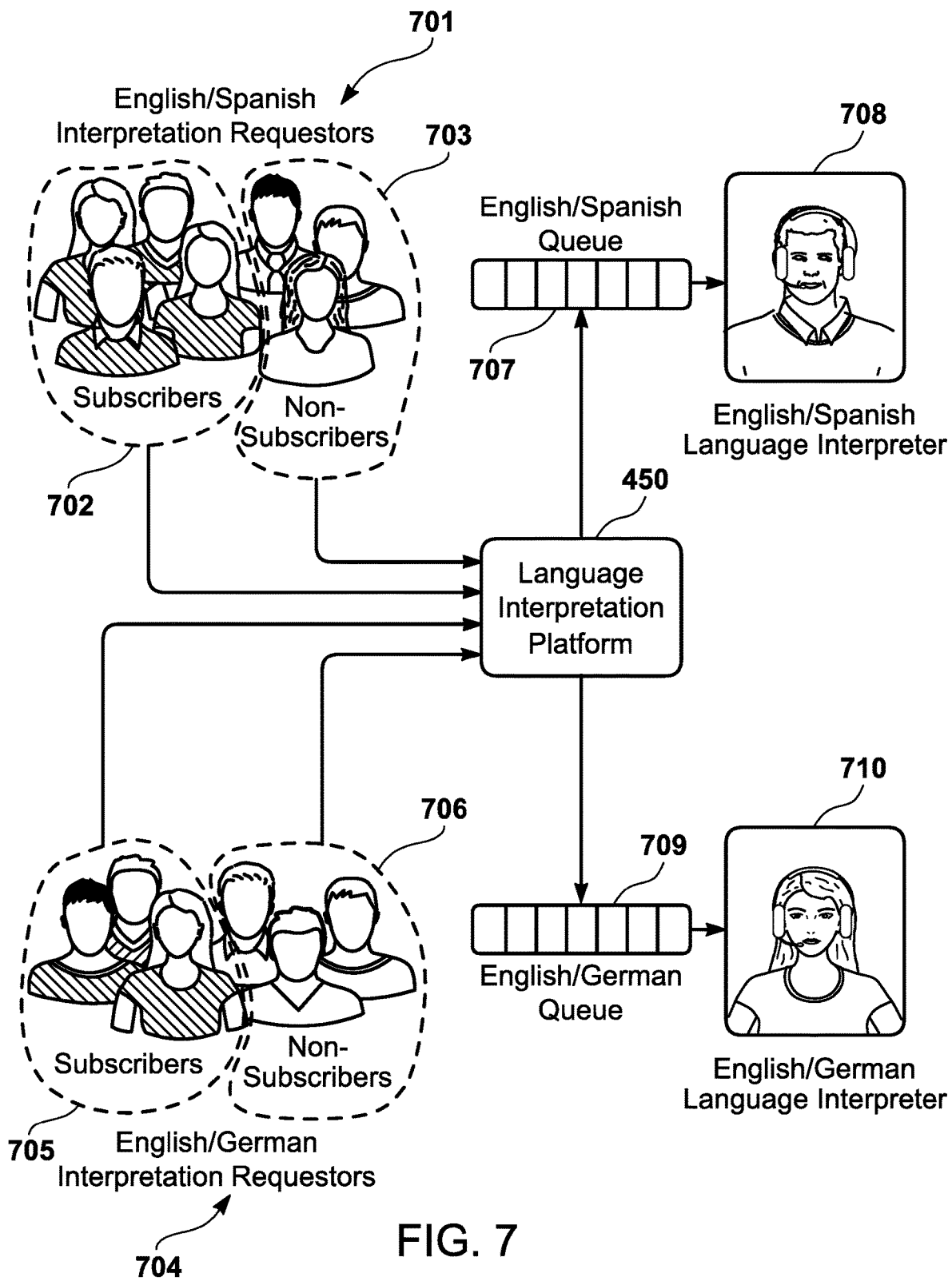
FIG. 7 illustrates the language interpretation platform, illustrated in FIG. 1, receiving language interpretation requests from multiple requestors speaking different languages.

As an example, FIG. 7 illustrates the language interpretation platform 450, illustrated in FIG. 1, receiving language interpretation requests from multiple requestors speaking different languages. For instance, a first group of users 701 may send requests via communication devices to the language interpretation platform 450 to obtain language interpretation from English to Spanish, and vice versa. The first group of users 701 may include both first group subscribers 702 and first group non-subscribers 703. Furthermore, a second group of users 704 may send requests via communication devices to the language interpretation platform 450 to obtain language interpretation from English to German, and vice versa. The second group of users 704 may include both second group subscribers 705 and second group non-subscribers 706. The language interpretation platform 450 receives interspersed language interpretation requests from the first group 701 and the second group 704, and routes each of the language interpretation request to a qualified, remotely situated language interpreter. For example, the language interpretation platform 450 may generate an English/Spanish queue 707 and route communications in that queue to one or more language interpreters 708 specifically qualified to perform language interpretation from English to Spanish, and vice-versa. Furthermore, the language interpretation platform 450 is able to retrieve the queue prioritization status, associated with each user, from the routing data structure 605, illustrated in FIG. 6, to properly insert a user's communication in the English/Spanish queue 707. For instance, the language interpretation platform 450, using the queue prioritization engine 606, may insert a language interpretation request from the first group subscribers 702 to a priority-based position within the English/Spanish queue 707, ahead of all of the first group non-subscribers 703 that may have previously called into the language interpretation platform 450. In essence, by having the queue prioritization status as a subscriber, a user in the first group subscribers 702 may have a faster connect time to an English/Spanish language interpreter 708 than those in the first group non-subscribers 703. Furthermore, a user in the second group subscribers 705 may have a faster connect time to an English/German language interpreter 710 than those in a second group non-subscribers 709 in a second queue 710. (Two queues are illustrated only as an example, given that many queues for different languages may be generated for different qualified language interpreters or groups of language interpreters.)

FIGS. 8A and 8B illustrate an example of a queue data structure 800 being used to store data corresponding to the English/Spanish queue 707 illustrated in FIG. 7. In particular, FIG. 8A illustrates the queue data structure 800 being a linked list in which one or more pointers are used to reference other data blocks; the sequence in which the pointers are arranged may denote the order in which requests in the English/Spanish queue 707 are handled by the English/Spanish language interpreter 708. Furthermore, for the sake of illustration, in this particular example, each of the current data blocks 802*a-c* corresponds to a non-subscriber request, and a data block 801 corresponding to the subscriber has not yet been inserted into the English/Spanish queue 707. Upon determining that the data block 801 corresponds to a subscriber, the queue prioritization engine 606, illustrated in FIG. 6, may insert the data block 801 at the front of the queue data structure 800 corresponding to the English/Spanish language interpreter 708, as illustrated in FIG. 8B; yet, such insertion may not be apparent to the non-subscribers corresponding to the current data blocks 802a-c. In other words, the queue prioritization engine 606 may seamlessly move the data block 801 to the front of the English/Spanish queue 707 without providing an alert to the non-subscribers of such insertion.

Furthermore, the queue data structure 800 improves the functioning of a computer because the insertion of the additional data block 801 at the front of the queue may be performed without modifying all of the remaining data blocks 802a-c. For example, a new pointer may be generated by the queue prioritization engine 606 to point from the current non-subscriber data block 802c at the front of the English/Spanish queue 707 to the subscriber data block 801, effectively prioritizing the subscriber communication to the front of the English/Spanish queue 707 without modifying more than one of the other data blocks in the English/Spanish queue 707. As a result, the queue data structure 800 is a data structure that is optimized to perform queue prioritization for language interpretation services. (A linked list is just one example of the queue data structure 800; other data structures may be used instead for the queue data structure 800.) Furthermore, less computing resources are necessary given that the entire queue data structure does not have to be modified.

FIGS. 9A and 9B illustrate an example of a queue data structure 900 being used to store data corresponding to the English/Spanish queue 707 illustrated in FIG. 7. In particular, FIG. 9A illustrates the queue data structure 900 being a linked list with both data blocks 802a-c corresponding to existing non-subscriber users and data blocks 901a and 901b corresponding to existing subscriber users within the English/Spanish queue 707. The data block 801 corresponding to the subscriber, who made a recent request, has not yet been inserted into the English/Spanish queue 707. Upon determining that the data block 801 corresponds to a subscriber, the queue prioritization engine 606, illustrated in FIG. 6, may insert the data block 801 in front of the non-subscriber data blocks 802a-c, but behind the existing subscriber data blocks 901a and 401b, as illustrated in FIG. 9B. Accordingly, in this instance, the additional subscriber was not prioritized to the front of the English/Spanish queue 707, but was prioritized to a priority-based position ahead of the non-subscribers, thereby resulting in a faster connect time to the English/Spanish language interpreter 708. In this instance, only the pointer on the data block 802c is modified to point to the data block 801, instead of the data block 901a, and a new pointer is generated to point from the data block 301 to the data block 901a. Therefore, computational resources are reduced, instead of having to be utilized for modifications to the entire queue data structure.

Although various configurations are described herein with respect to human-spoken languages, the configurations provided for herein may additionally, or alternatively, be used for other forms of communication (e.g., sign language).

It is understood that the apparatuses, systems, computer program products, and processes described herein may also be applied in other types of apparatuses, systems, computer program products, and processes. Those skilled in the art will appreciate that the various adaptations and modifications of the embodiments of the apparatuses, systems, computer program products, and processes described herein may be configured without departing from the scope and spirit of the present apparatuses, systems, computer program products, and processes. Therefore, it is to be understood that, within the scope of the appended claims, the present apparatuses, systems, computer program products, and processes may be practiced other than as specifically described herein.

We claim:

1. A computer program product comprising a non-transitory computer readable storage device having a computer readable program stored thereon, wherein the computer readable program when executed on a computer causes the computer to:

generate, at a language interpretation platform, a graphical user interface that manages a connection time between a user-operated device and a language interpreter-operated device, the graphical user interface displaying a language pair menu of language pairs available for language interpretation, an availability indicium that indicates a non-prioritized time in which a language interpreter is available to perform a language interpretation of the language pair, and a prioritization indicium that, via activation, prioritizes the language interpretation according to a prioritized time that is faster than the non-prioritized time;

receive, from the graphical user interface of the user-operated device, a request for a live language interpretation session;

determine, from the activation of the prioritization indicium in the graphical user interface of the user-operated device, an activation of a queue prioritization status, the activation being selected from the group consisting of: an automatic account activation, a user-inputted activation via a virtual indicium in the graphical user interface, and an environmental activation; and assign, to the graphical user interface of the user-operated device, the prioritization status to the user-operated device to prioritize the connection time in a queue of waiting devices.

2. The computer program product of claim 1, wherein the automatic account activation is a fee-based subscription account configuration that is established prior to the live language interpretation session.

3. The computer program product of claim 1, wherein the user-inputted activation is a fee-based activation associated with a prioritization fee, the prioritization fee being higher than a fee associated with the live language interpretation session.

4. The computer program product of claim 1, wherein the user-inputted activation is an emergency-based activation associated with an emergency in a geographical area.

5. The computer program product of claim 4, wherein the computer is further caused to perform an environmental assessment to validate that the user-operated device is positioned within the geographical area.

6. The computer program product of claim 1, wherein the environmental activation is an emergency-based activation associated with an emergency in a geographical area.

7. The computer program product of claim 6, wherein the computer is further caused to receive data from an external source other than the user-operated device to automatically determine an occurrence of the emergency and automatically perform the environmental activation without an additional user input at the graphical user interface.

8. The computer program product of claim 1, wherein the live language interpretation session is a video remote interpretation session.

9. The computer program product of claim 1, wherein the live language interpretation session is an over the phone interpretation session.

10. A method comprising:
generating, at a language interpretation platform, a graphical user interface that manages a connection time between a user-operated device and a language interpreter-operated device, the graphical user interface displaying a language pair menu of language pairs available for language interpretation, an availability indicium that indicates a non-prioritized time in which a language interpreter is available to perform a language interpretation of the language pair, and a prioritization indicium that, via activation, prioritizes the language interpretation according to a prioritized time that is faster than the non-prioritized time;
receiving, from the graphical user interface of the user-operated device, a request for a live language interpretation session;
determining, from the activation of the prioritization indicium in the graphical user interface of the user-operated device, an activation of a queue prioritization status, the activation being selected from the group consisting of: an automatic account activation, a user-inputted activation via a virtual indicium in the graphical user interface, and an environmental activation; and
assigning, to the graphical user interface of the user-operated device, the prioritization status to the user-operated device to prioritize the connection time in a queue of waiting devices.

11. The method of claim 10, wherein the automatic account activation is a fee-based subscription account configuration that is established prior to the live language interpretation session.

12. The method of claim 10, wherein the user-inputted activation is a fee-based activation associated with a prioritization fee, the prioritization fee being higher than a fee associated with the live language interpretation session.

13. The method of claim 10, wherein the user-inputted activation is an emergency-based activation associated with an emergency in a geographical area.

14. The method of claim 13, further comprising performing an environmental assessment to validate that the user-operated device is positioned within the geographical area.

15. The method of claim 10, wherein the environmental activation is an emergency-based activation associated with an emergency in a geographical area.

16. The method of claim 15, wherein the computer is further caused to receive data from an external source other than the user-operated device to automatically determine an occurrence of the emergency and automatically perform the environmental activation without an additional user input at the graphical user interface.

17. The method of claim 10, wherein the live language interpretation session is a video remote interpretation session.

18. The method of claim 10, wherein the live language interpretation session is an over the phone interpretation session.

19. A mobile computing device comprising:
a processor that generates a graphical user interface that manages a connection time with a language interpreter-operated device, the processor determining an activation of a queue prioritization status from a prioritization indicium in the graphical user interface, the activation being selected from the group consisting of: an automatic account activation, a user-inputted activation via a virtual indicium in the graphical user interface, and an environmental activation;
a display device that renders the graphical user interface such that the graphical user interface displays a language pair menu of language pairs available for language interpretation, an availability indicium that indicates a non-prioritized time in which a language interpreter is available to perform a language interpretation of the language pair, and the prioritization indicium that, via activation, prioritizes the language interpretation according to a prioritized time that is faster than the non-prioritized time;
a transmitter that transmits a request for a live language interpretation session to a language interpretation platform; and
a receiver that receives the prioritization status to the user-operated device to prioritize the connection time in a queue of waiting devices.

20. The mobile computing device of claim 19, wherein the automatic account activation is a fee-based subscription account configuration that is established prior to the live language interpretation session.

* * * * *